United States Patent [19]
Freud et al.

[11] Patent Number: 5,485,270
[45] Date of Patent: Jan. 16, 1996

[54] DYNAMIC LIGHT SCATTERING MICROVOLUME CELL ASSEMBLY FOR CONTINUOUS FLOW DIALYSIS

[75] Inventors: Paul J. Freud, Furlong, Pa.; Clarissa G. Jakob, Columbia, S.C.

[73] Assignee: General Signal Corporation, New York, N.Y.

[21] Appl. No.: 279,992

[22] Filed: Jul. 25, 1994

[51] Int. Cl.[6] ................................................ G01N 21/05
[52] U.S. Cl. ........................ 356/336; 356/246; 356/342
[58] Field of Search .................................. 356/336, 338, 356/342, 246

[56] References Cited

U.S. PATENT DOCUMENTS

| | | | |
|---|---|---|---|
| 4,242,194 | 12/1980 | Steiner et al. | 356/39 |
| 4,819,478 | 4/1989 | Melcher | 73/61.1 |
| 4,975,237 | 12/1990 | Brown | 356/338 |
| 4,983,040 | 1/1991 | Chu et al. | 356/338 |
| 5,094,526 | 3/1992 | Freud et al. | 356/28.5 |
| 5,108,907 | 4/1992 | Pleass et al. | 435/34 |
| 5,155,549 | 10/1992 | Dhadwal | 356/336 |
| 5,286,452 | 2/1994 | Hansen | 422/73 |
| 5,372,783 | 12/1994 | Lackie | 356/246 |

*Primary Examiner*—Richard A. Rosenberger
*Attorney, Agent, or Firm*—Ohlandt, Greeley, Ruggiero & Perle

[57] ABSTRACT

A dynamic light scattering analyzer which comprises: a sample cell which comprises a cell housing and a cell chamber, the cell chamber being formed within the cell housing such that the cell chamber is exposed to a membrane which is capable of retaining within the cell chamber the particles of a sample introduced into the cell chamber while allowing a liquid carrier to diffuse across the membrane in and out of the cell chamber; a light source; an optical waveguide which is capable of exposing the particles to a light source and which is capable of receiving the light scattered from the particles within the cell chamber and the light reflected from the waveguide-solution interface; a photodetector which is capable of detecting the light scattered from the particles within the cell chamber and the light reflected from the waveguide-solution interface; and a pump for controlling the flow rate and concentration of the carrier liquid which contacts the membrane.

26 Claims, 5 Drawing Sheets

DYNAMIC LIGHT SCATTERING MICROVOLUME CELL ASSEMBLY FOR CONTINUOUS FLOW DIALYSIS

The present invention relates generally to a dynamic light scattering analyzer which is capable of measuring the size of particles (e.g., crystallized protein molecules) contained within a small sample (i.e., microvolume) cell. In particular, the sample is retained within a cell chamber by means of a dialysis membrane (or other type of membrane) while a continuous flow fluid, such as inhibitors, substrates, salts, etc, is selectively dialyzed in and out of the cell chamber, thereby allowing in-situ adjustment to the concentration of the sample, or its components, together with continuous dynamic light scattering analysis thereof.

BACKGROUND OF THE INVENTION

Dynamic light scattering (DLS) is a well established technique for measuring particle size over the size range of a few nanometers to a few microns. DLS determines particle size from the analysis of the Brownian motion of suspended particles. Light scattered from a moving particle has a Doppler light frequency shift imparted to it. Scattering from a group of particles will have a distribution of shifts from the randomly moving particles. Measuring the Doppler shifts therefore provides a means of measuring the Brownian motion of the particles and hence provides a means of determining the size of the particles.

Most fine particle size analyzers determine particle size by measuring the Doppler shift of light as it is scattered by moving particles. Smaller particles move faster, causing a greater Doppler shift in the light they scatter. With conventional analyzers, light passes completely through an extremely dilute suspension and scatters in all directions. The detector measuring the Doppler shifts of the scattered light has no high-level signal to reference against. The resulting low-level signals require amplification from photomultipliers, which can introduce noise errors.

In the Microtrac® ultrafine particle analyzer (sold by Leeds & Northrup, a unit of General Signal Corporation), light travels to the sample via an optical wave guide. A mirror reflects some of the light, creating a high-level reference signal. Moving particles back-scatter the light penetrating the mirror. The Microtrac® ultrafine particle analyzer combines the reflected and back-scattered light to create a high-level signal strong enough to be fed directly to a reliable solid-state photodetector.

The Microtrac® ultrafine particle analyzer is typically operated such that a stream of liquid carrier containing the particles to be analyzed are sent past a photoprobe (e.g., an optical probe). If the solution containing the particles to be analyzed did not produce the desired result, other solutions would be produced and sent past the photoprobe until an acceptable result is obtained. This procedure is acceptable for solutions which are inexpensive and readily available. However, in the case where the solutions to be passed by the photoprobe are relatively expensive, it would not be desirable to continuously send new solutions into the sample cell until the desired results are obtained. This is particularly true in the case of proteins wherein the high cost of the material substantially outweighs the information obtained by conducting dynamic light scattering analysis of the particles contained therein. Accordingly, biochemical researchers have foregone the DLS analysis of proteins and other expensive particles due to their high cost and the need by conventional DLS analyzers to use substantial volumes of solution containing such particles in order to arrive at acceptable results.

It would be most desirable to be able to perform DLS analysis of proteins and other expensive materials, without using large sample volumes. The present inventors have developed a unique DLS analyzer which uses a small volume sample for measurement of particle size, while allowing for the in-situ adjustment of the concentration of each sample using inexpensive continuous flow fluids, such as inhibitors, substrates, salts, etc. As such, the concentration of the sample can be gradually changed while it is continuously analyzed, without having to continuously replace the sample volume if the results obtained are not acceptable.

Several very important areas of protein research can benefit from this DLS analysis having continuous flow dialysis. Prior to the present invention, DLS technology had been primarily applied only to "model" proteins which are available in huge quantities and at low cost in order to prove its benefits to protein research. The present invention allows the use of DLS technology in three major areas of macromolecular research which would not otherwise be able to take advantage of this kind of analysis, i.e., protein subunit oligomerization, enzyme/enzyme interactions, and protein aggregation/crystallization.

Without a continuous flow set-up such as the present invention, DLS technology is too sample costly to be routinely used in protein research. DLS systems presently available require too large of a sample volume, too high sample concentration, and multiple sample handlings for each data point collected. Also, in order to collect multiple data points, large amounts of research time are required. The continuous flow dialysis approach of the present invention would require only one sample handling step and would save research time by allowing the computer to automatically change sample components and collect the necessary data in a single or multidimensional manner.

The ability to adjust and alter the liquid carrier in the cell chamber has several advantages: lower sample loss, less sample preparation time, virtually continuous sample monitoring, and automated analysis.

The present invention also provides many additional advantages which shall become apparent as described below.

SUMMARY OF THE INVENTION

A sample cell for use in a dynamic light scattering assembly which comprises a cell housing and a cell chamber, the cell chamber being formed within the cell housing such that the cell chamber is exposed to a membrane which is capable of retaining within the cell chamber the particles of a sample introduced into the cell chamber while allowing a liquid carrier to diffuse across the membrane in and out of the cell chamber.

The membrane used in the cell chamber is preferably a dialysis membrane, although any membrane which is capable of allowing the liquid carrier (i.e., the continuous flow fluid) to diffuse back and forth across the membrane while preventing the diffusion of the particles within the cell chamber is also contemplated hereby. The membrane is preferably a cellulose membrane.

The sample cell also preferably includes a means for controlling the temperature of the sample disposed within the cell chamber. The means for controlling the temperature is a water jacket disposed about the cell chamber.

The unique sample cell of the present invention is preferably used in a dynamic light scattering analyzer which comprises: a sample cell which comprises a cell housing and a cell chamber, the cell chamber being formed within the cell housing such that the cell chamber is exposed to a membrane which is capable of retaining within the cell chamber the particles of a sample introduced into the cell chamber while allowing a liquid carrier to diffuse across the membrane in and out of the cell chamber; a light source; a means for exposing the particles to a light source; a means for receiving the light scattered from the particles within the cell chamber and the light reflected from the waveguide-solution interface (i.e., light source-sample interface); a means of detecting the amount of light scattered from the particles within the cell chamber and light reflected from the waveguide-solution interface (i.e., light source-sample interface); and a means for controlling the flow rate and concentration of the carrier liquid which contacts the membrane.

The means for exposing the particles to a light source is an integrated optical waveguide which is capable of emitting light from the light source into the cell chamber. The light source is preferably a laser diode. The means for receiving the light scattered from the particles within the cell chamber and the light reflected from the waveguide-solution interface is typically the same integrated optical waveguide used to emit the light source. The detecting means is a photodetector, e.g., a silicon photodetector.

The means for controlling the flow rate and concentration of the carrier liquid is a pump means and a microprocessor. The microprocessor is also connected to the light source to control the amount of light which is emitted into the cell chamber. The microprocessor is also connected to the detecting means so as to collect and store data transmitted from the detecting means.

The present invention also encompasses a photodetector probe assembly which comprises: a housing; a cell chamber disposed within the end of the housing which is in contact with a liquid carrier, wherein the cell chamber is formed by affixing a membrane to the end of the housing, the membrane is one which is capable of retaining therein particles of a sample contained within the cell chamber while allowing the liquid carrier to diffuse across the membrane in and out of the cell chamber; a light source; a means for exposing the particles to a light source; a means for receiving the light scattered from the particles within the cell chamber and the light reflected from the waveguide-solution interface; a means of detecting the amount of light scattered from the particles within the cell chamber and light reflected from the waveguide-solution interface.

Other and further objects, advantages and features of the present invention will be understood by reference to the following specification in conjunction with the annexed drawings, wherein like parts have been given like numbers.

DESCRIPTION OF THE PREFERRED EMBODIMENTS

In dynamic light scattering analysis an optical beam emerging from an optical waveguide into a suspension of particles is scattered by the particles. The back scattered light is collected by the waveguide and transmitted back through the guide. A second component of light is also transmitted back through the guide as the result of the reflection at the interface between the guide tip and the suspending medium. If these two components being transmitted back through the guide are coherent, they will interfere with each other and result in a component of signal which has the different frequencies between the reflected and scattered components. The different frequencies are the same as the desired Doppler frequency shifts. The reflected beam acts as an unshifted reference and the scattered beams has the set of Doppler shifts as the result of scattering from the moving particles.

A critical requirement of the measurement system is the complete directional separation of the forward and reverse beams. An optical surface waveguide with a Y-splitter efficiently separates the forward and reverse beams and provides the interface with the particle suspension, all on a stable common substrate. The use of the optical surface waveguide is particularly useful in detecting particles sizes for small sample amount. This optical waveguide is discussed in detail in U.S. Pat. No. 5,094,526 (Freud et al.), which issued on Mar. 10, 1992, and which is incorporated herein by reference.

The optical waveguide is connected to a laser diode which provides the light source and a silicon photodiode which receives the return signal. The return signal is the product of the light scattered from the particles within the cell chamber and light reflected from the waveguide-solution interface, and is strong enough to use the photodiode for detection.

The received signal resembles random noise at the output of the silicon photodiode as the result of the mixing of the Doppler shifts from all the particles scattering the laser light. The photodiode output is digitized and with a digital signal processor, the power spectrum of the signal is determined using Fast Fourier Transform techniques. The power spectrum is the function which is analyzed to determine the particle size distribution.

Figure 1:
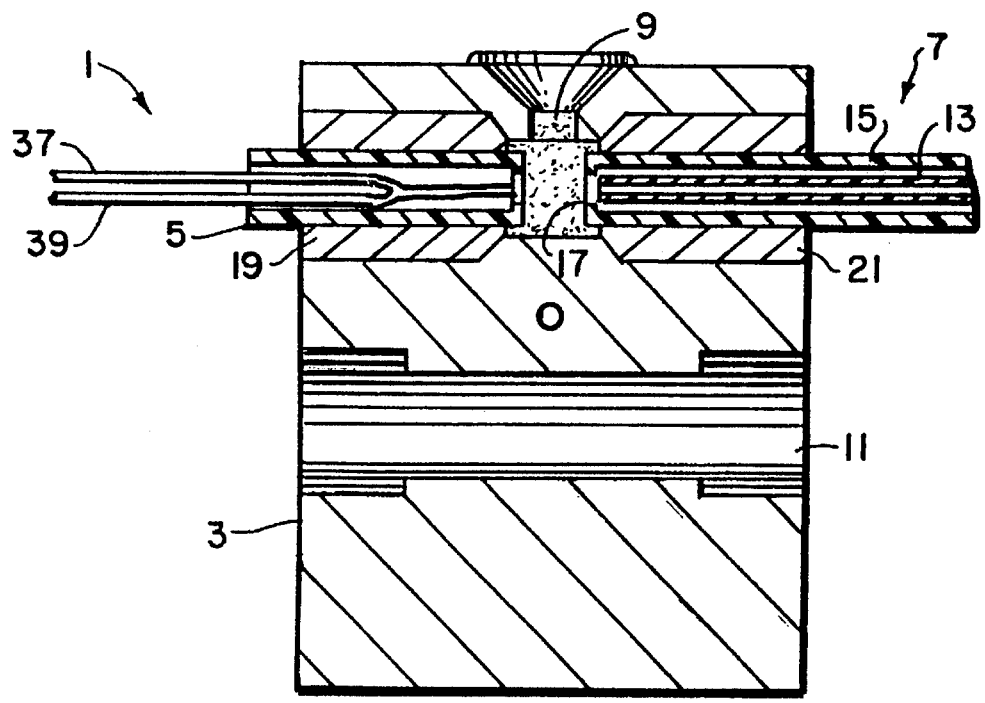
FIG. 1 is a schematic representation of an ultrafine particle analyzer assembly according to one embodiment of the present invention wherein a cell chamber is disposed between an optical waveguide probe and a coaxial liquid carrier conduit having a dialyzing membrane disposed at the end in contact with the cell chamber.
Figure 2:
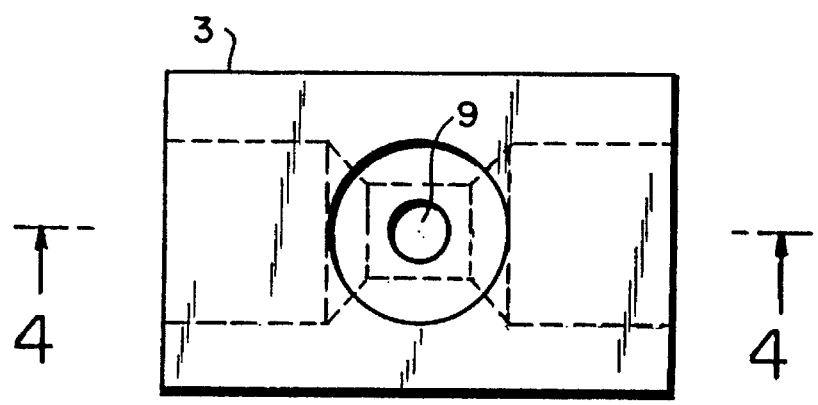
FIG. 2 is a top planar view of the ultrafine particle analyzer assembly shown in FIG. 1.
Figure 4:
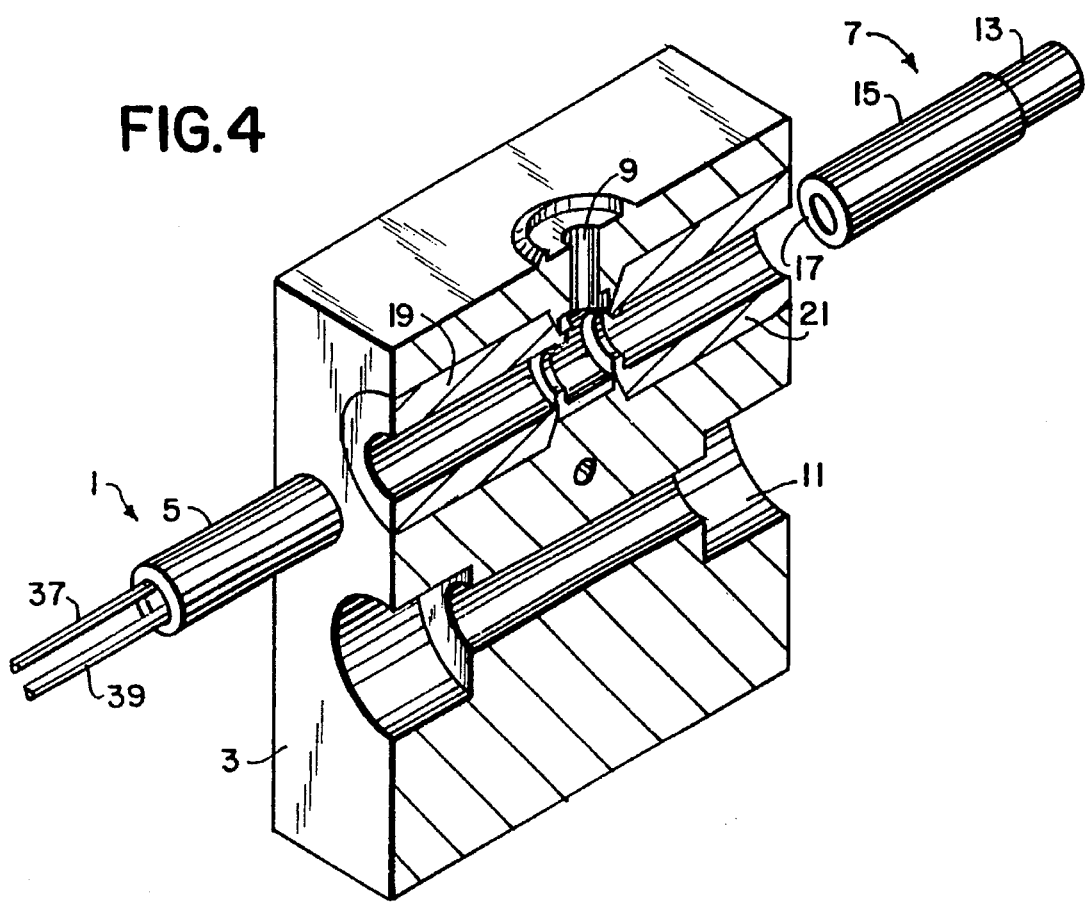
FIG. 4 is an exploded front right perspective view of the ultrafine particle analyzer assembly shown in FIG. 1.

FIGS. 1, 2 and 4 depict an ultrafine particle analyzer assembly 1 comprising a 316 stainless steel housing 3, an optical probe 5 with an optical waveguide, a continuous flow fluid or liquid carrier probe 7, and a cell chamber 9 disposed between optical probe 5 and continuous flow fluid probe 7.

Cell chamber 9 has a gap of approximately 3 millimeters between opposing ends of optical probe 5 and continuous flow fluid probe 7. Also disposed within housing 3 is a through-hole 11 which allows a liquid or gas to pass therethrough so as to control the temperature of the solution contained within cell chamber 9. It is preferable that through-hole 11 be a water jacket or the like. Continuous flow fluid probe 7 comprises a coaxial fluid conduit and a membrane 17. The coaxial fluid conduit comprises an inner conduit 13 and an outer conduit 15, the outer conduit 15 being centrally disposed about inner conduit 13. By having membrane 17 disposed on the tip of continuous flow fluid probe 7, the continuous flow fluid or liquid carrier is capable of entering cell chamber 9 from inner conduit 13 by diffusion through membrane 17. The continuous flow fluid or liquid carrier eventually equilibrates with the sample fluid in cell chamber 9 without exchanging sample particles. That is, the sample particles that are initially disposed within cell chamber 9 are retained therein by means of membrane 17. As fluid enters cell chamber 9 by diffusion across membrane 17, a similar volume of fluid back-diffuses across membrane 17 and exits ultrafine particle analyzer assembly via outer conduit 15.

Optical probe 5 and continuous flow fluid probe 7 can be positioned with a controlled gap between them thus controlling the volume of the sample which is required for proper particle size measurement. It is preferable that optical probe 5 and fluid probe 7 be positioned within assembly 1 such that their respective ends are 0.5 to 5 millimeters apart. Moreover, the ports within the sidewalls of cell chamber 9 which secure probes 5 and 7 to assembly 1 have a diameter in the range of about 5–10 millimeters. Probes 5 and 7 are securely affixed to assembly 1 by means of ferrule or other seal-tight fittings 19 and 21, respectively. The preferred total same volume required to fill the cavity or cell chamber is 0.01 to 0.4 milliliters. Conversely, the conventional cell chamber for the ultrafine particle analyzer is 5 milliliters, i.e., approximately 10 to 500 times more than the sample volume. The equilibration across membrane 17 also benefits from the small volume of the cell chamber, since the time for equilibration will be proportional to the volume being equilibrated. Thus, membrane 17 allow for the analytical technician to adjust the concentration of the sample volume in-situ until an acceptable result is obtained and the particle size is correctly measured. It is preferable that the continuous flow fluid or carrier liquid be either an inhibitor, a substrate, a salt (e.g., $NaCl.(NH_4)_2SO_4$) or other fluids such as organic solvents.

Figure 6:
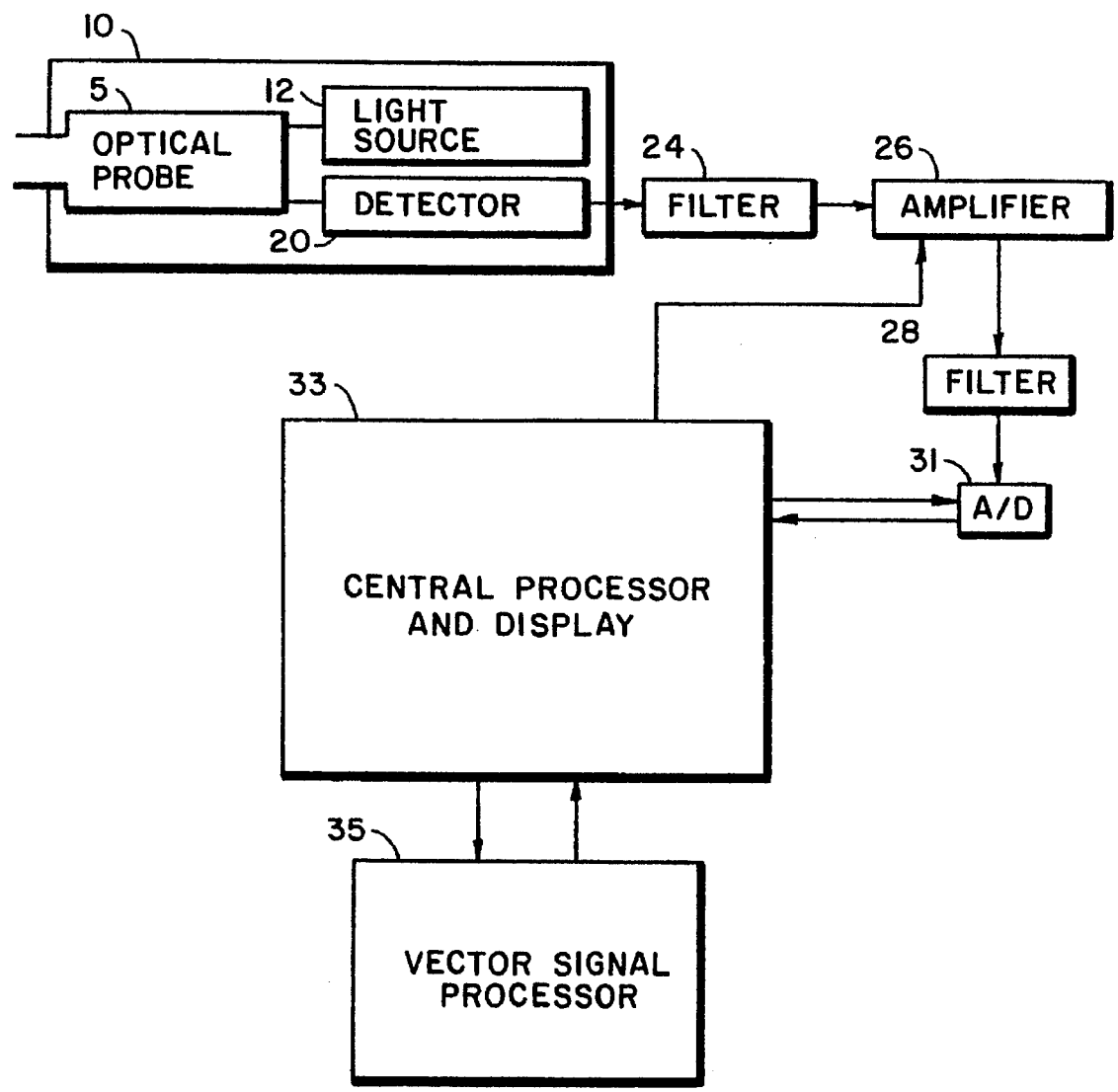
FIG. 6 shows in block diagram form the Doppler velocimeter of the present invention as part of an apparatus for measuring particle size and distribution.

A typical Doppler velocimeter used in accordance with the present invention is shown in FIG. 6, wherein Doppler velocimeter 10 includes a laser diode light source 12 which transmits a beam of light into an optical probe 5. Optical probe 5 is mounted in the side of a sample cell assembly 1 holding particulate matter suspended in a carrier liquid. Although optical probe 5 may be mounted in a number of different positions, in a preferred embodiment it is mounted horizontally in the sidewall of cell chamber 9 so that the end of probe 5 is adjacent the carrier liquid having moving surfaces therein to be measured.

The detector 20 generates a signal the magnitude of which varies with time and is indicative of the difference in frequency between the light scattered from the particles within cell chamber 9 and the light reflected from the waveguide-solution interface. The output signal from detector 20 is transmitted to a direct current blocking filter 24 to remove the direct current component of the signal that is introduced by detector 20. The output from filter 24 is amplified by a low noise amplifier 26 having a gain which is selectable. The output of amplifier 26 is connected to a filter 28 whose output is in turn connected to an analog to digital converter 31. Filter 28 is preferably a 20 kHz active filter which serves as an anti-aliasing filter for analog to digital converter 31. Filter 28 serves to remove all frequency components of the signal which are above ½ the sampling rate. Analog to digital converter 31 converts the analog signal amplified at amplifier 26 and filtered in filter 28 into a format that can be easily processed by computer 33. Analog to digital converter 31 preferably operates at a sampling rate of 50 kHz.

Analog to digital converter 31 is connected to a central processor 33. Also connected to central processor 33 is a vector signal processor 35 preferably of the type manufactured by Burr-Brown under Model No. ZPB32-H5. Signal processor 35 generates a signal which represents the power spectrum of the signal delivered to computer 33 by analog to digital converter 31.

Figure 7:
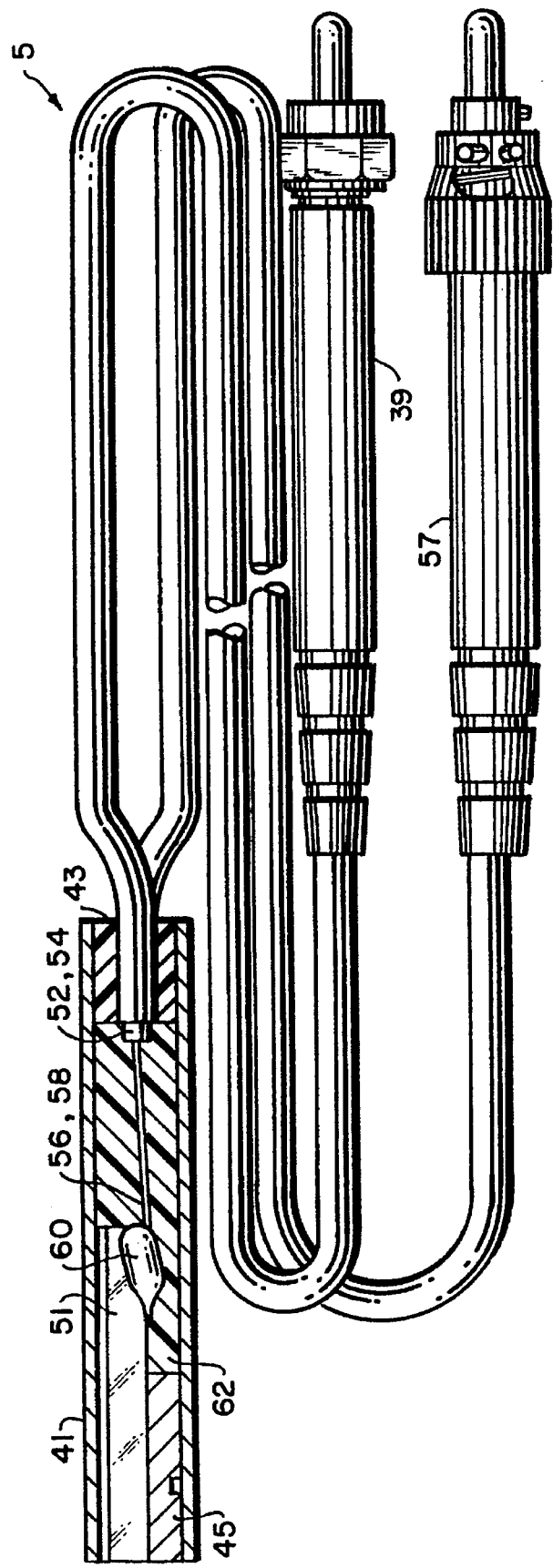
FIG. 7 shows in partial cross-section, a probe and fiber optic cable assembly forming a part of the Doppler velocimeter of the present invention.

Referring to FIG. 7, probe 5 includes a fiber optic cable 37 adapted to receive an incident beam of light from light source 12 and a fiber optic cable 39 for delivering the reflected light signal to detector 20. Probe 5 further includes a tubular housing 40 preferably made of stainless steel, for protecting all delicate probe components. A suitable hard epoxy compound 43 bounds the end of fiber optic cables 37 and 39. A stainless steel support piece 45 is engaged in a force fitting relationship at the other end of housing 41 and includes a slot extending the length thereof. An integrated optical waveguide 51 is supported within the slot by support member 45. As used herein, the term "integrated optical waveguide" is intended to mean one or more optical waveguide paths supported by and integral with a common substrate. A pair of polyester tubes 52 and 54 extend from cables 37 and 39, respectively. In addition, optical fibers 56 and 58 contained within tubes 52 and 54, respectively, are secured to integrated optical waveguide 51 by an epoxy cement 60. A silicone grease 62 fills the center of housing 41 to protect the internal components from moisture.

Figure 3:
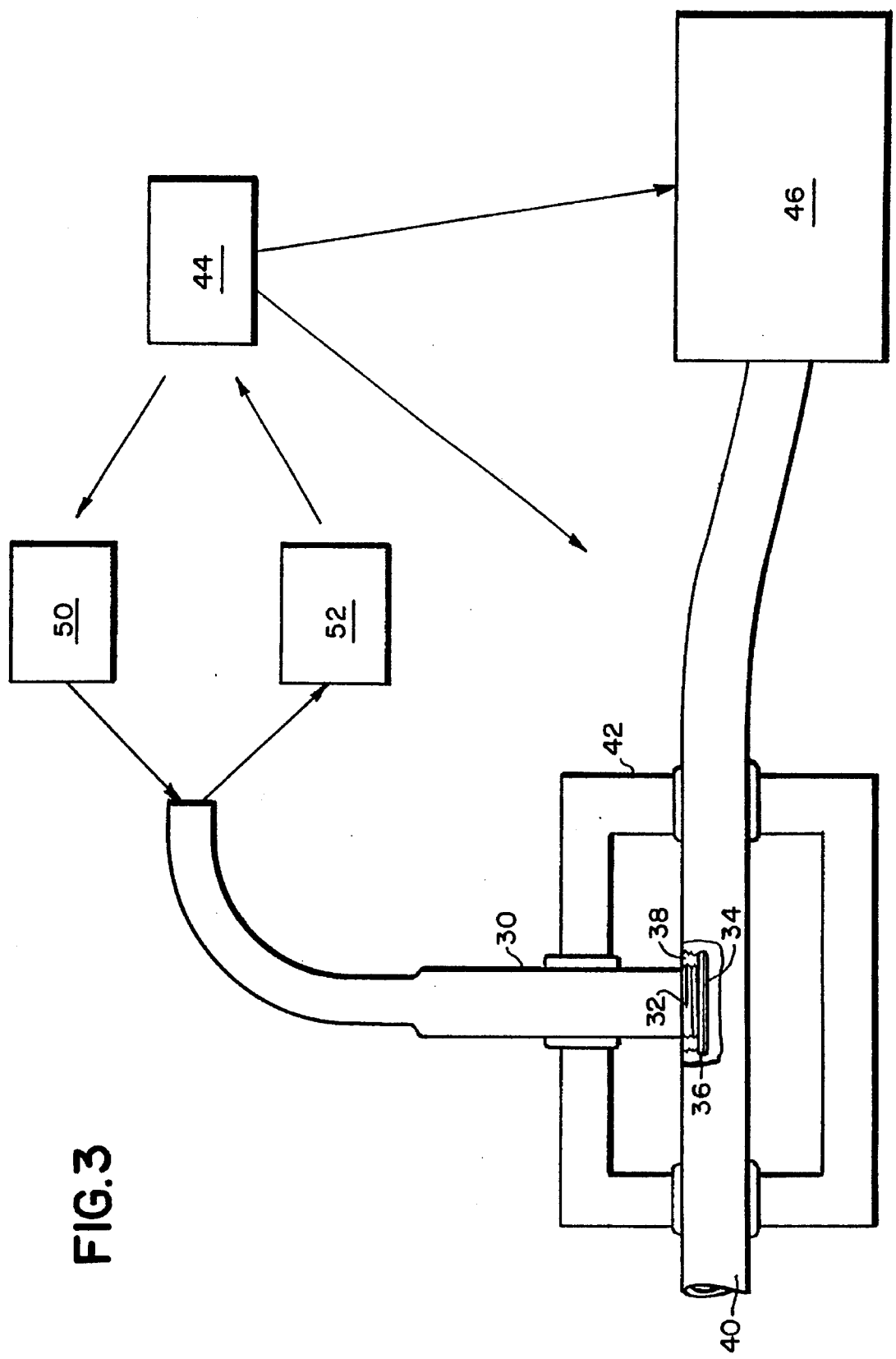
FIG. 3 is a schematic representation of an ultrafine particle analyzer system according to another embodiment of the present invention wherein a cell chamber is located within an optical probe assembly wherein the particles are retained therein by means of a membrane disposed about the bottom of the probe.
Figure 5:
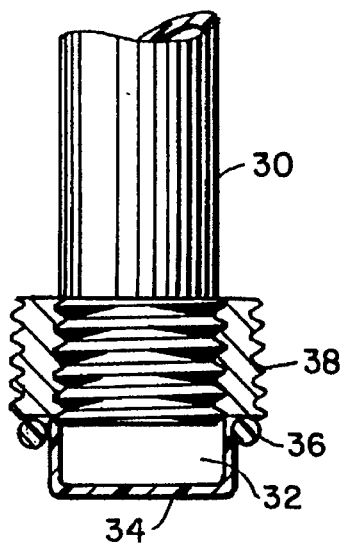
FIG. 5 is a detailed view of the cell chamber and membrane disposed about one end of optical probe assembly shown in FIG. 3.

FIGS. 3 and 5 depict another embodiment of the present invention wherein the photoprobe 30 is designed such that cell chamber 32 is formed at the end portion of photoprobe 30. Cell chamber 32 is formed by affixing a dialysis membrane 34 of the appropriate molecular weight cut-off to the bottom of a screw-type fitting 38. Membrane 34 is affixed to screw-type fitting 38 by means of a rubber o-ring 36. As such, a protein sample (about 0.02 milliliters) is then be placed in cell chamber 32 which is then attached to photoprobe 30 using screw-type fitting 38. The use of a ferrule or other seal-tight connector may also be needed.

Thereafter, photoprobe 30 containing cell chamber 32 can be inserted into a stream of continuously flowing fluid or carrier liquid passing through conduit 40. Photoprobe 30 is preferably affixed to the sidewall of conduit 40 by a screw tight connection. Conduit 40 preferably passes through a temperature controlled environment such as a constant temperature box 42.

Optical probe 30, which comprises a cell chamber 34, eliminates multiple sample preparation and handling by taking advantage of the sample particle's (e.g., protein molecule) molecular weight. Dialysis membrane 32 retains the sample particles within cell chamber 32 while at the same time allowing smaller molecules like inhibitors, substrates, salts, etc. to be selectively dialyzed in and out of cell chamber 34. The sample components are controlled using a multicomponent gradient pump 46 to change the composition of the dialysate or carrier liquid.

In operation, DLS photoprobe 30 according to the present invention retains the protein particles within cell chamber 32 by means of dialysis membrane 34. Dialysate or carrier liquid is pumped via pump means 46 into conduit 40 such that it comes into contact with membrane 34. The dialysate diffuses through membrane 34 in and out of cell chamber 32. The temperature, dialysate concentration and light emission (i.e., emission from laser diode 50) is preferably controlled by microprocessor 44. Microprocessor 44 is also used for control data collection and storage from detector 52.

This DLS photoprobe assembly is very versatile and has applications other than just continuous flow dialysis. For example, a simple plastic cup-like sample cell can be used for routine static monomode analysis of small or valuable samples. The sample cell would be disposable and the photoprobe could be easily cleaned between samples. For samples available in larger quantities, a beaker or the like could be used as the sample cell.

The most widely used technique for determining the high resolution 3-D structure of a protein is protein crystallography combined with x-ray diffraction techniques. In order to determine the structure of a protein, one must first obtain high quality protein crystals. The majority of protein crystals are grown by the hanging drop vapor diffusion method using standard 24 well tissue culture plates or 24 well Linbro plates. In a typical experiment, approximately 0.5 milliliters of a precipitating agent would be placed in the well of the tissue culture plate, then 0.005 milliliters of the precipitating agent and 0.005 milliliters of protein solution would be placed on a siliconized cover glass. The cover glass would be inverted and sealed over the well containing precipitating agent using ordinary high vacuum grease. Because the concentration of the precipitating agent is lower in the droplet than in the well, over the next few days, water vapor will diffuse from the droplet to the well. The net effect is a slow increase in the concentration of the precipitating agent in the drop which will hopefully lead to crystal formation in the droplet hanging from the cover glass.

It has become increasingly important for protein crystallographers to monitor crystallization experiments as the crystals form. The DLS photoprobe assembly according to the present invention would be most suitable for routine crystallization monitoring in the laboratory and in outerspace.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A sample cell for use in a dynamic light scattering assembly which is capable of measuring the size of particles contained within said sample cell, said sample cell comprises:
    a cell housing;
    a cell chamber, said cell chamber being formed within said cell housing such that said cell chamber is exposed to a membrane which is capable of retaining within said cell chamber the particles of a sample introduced into said cell chamber while allowing a liquid carrier to diffuse across said membrane in and out of said cell chamber; and
    a means for exposing said particles contained within said cell chamber to a light source, said means for exposing being disposed substantially opposite said membrane.

2. The sample cell according to claim 1 wherein said membrane is a dialysis membrane.

3. The sample cell according to claim 1 wherein said membrane is a cellulose membrane.

4. The sample cell according to claim 1 wherein said means for exposing said particles contained within said cell chamber to a light source is an integrated optical waveguide which is capable of both emitting light from said light source into said cell chamber and receiving light scattered from said particles within said cell chamber and light reflected from the light source-sample interface.

5. The sample cell according to claim 1 wherein a gap in the range between about 0.5 to 5 millimeters is formed between said means for exposing said cell chamber to a light source and said membrane.

6. The sample cell according to claim 1 further comprising a coaxial conduit disposed on the side of said membrane which is opposite said cell chamber.

7. The sample cell according to claim 6 wherein said coaxial conduit comprises an outer conduit centrally disposed about an inner conduit.

8. The sample cell according to claim 1 further comprising a means for controlling the temperature of the sample disposed within said cell chamber.

9. The sample cell according to claim 8 wherein said means for controlling the temperature is a water jacket disposed about said cell chamber.

10. A dynamic light scattering analyzer which is capable of measuring the size of particles contained within said dynamic light scattering analyzer, said dynamic light scattering analyzer comprises:
    a sample cell which comprises a cell housing and a cell chamber, said cell chamber being formed within said cell housing such that said cell chamber is exposed to a membrane which is capable of retaining within said cell chamber the particles of a sample introduced into said cell chamber while allowing a liquid carrier to diffuse across said membrane in and out of said cell chamber;
    a light source;
    a means for exposing said particles to a light source, said means for exposing being disposed substantially opposite said membrane;
    a means for receiving the light scattered from said particles within said cell chamber and the light reflected from the light source-sample interface;
    a means of detecting the amount of light scattered from said particles within said cell chamber and light reflected from the light source-sample interface; and
    a means for controlling the flow rate and concentration of said carrier liquid which contacts said membrane.

11. The dynamic light scattering analyzer according to claim 10 further comprising a means for controlling the temperature of said sample.

12. The dynamic light scattering analyzer according to claim 11 wherein said means for controlling the temperature of said sample is a water jacket disposed about said cell chamber.

13. The dynamic light scattering analyzer according to claim 10 wherein said means for exposing said particles to a light source is an integrated optical waveguide which is capable of emitting light from said light source into said cell chamber.

14. The dynamic light scattering analyzer according to claim 10 wherein said light source is a laser diode.

15. The dynamic light scattering analyzer according to claim 10 wherein said means for receiving the light scattered from said particles within said cell chamber and the light reflected from the light source-sample interface is an integrated optical waveguide.

16. The dynamic light scattering analyzer according to claim 10 wherein said detecting means is a photodetector.

17. The dynamic light scattering analyzer according to claim 16 wherein said photodetector is a silicon photodetector.

18. The dynamic light scattering analyzer according to claim 10 wherein said means for controlling the flow rate and concentration of said carrier liquid is a pump means and a microprocessor.

19. The dynamic light scattering analyzer according to claim 10 further comprising a microprocessor connected to said light source to control the amount of light which is emitted into said cell chamber.

20. The dynamic light scattering analyzer according to claim 10 further comprising a microprocessor connected to said detecting means so as to collect and store data transmitted from said detecting means.

21. The dynamic light scattering analyzer according to claim 10 wherein said membrane is a dialysis membrane.

22. The dynamic light scattering analyzer according to claim 10 wherein said membrane is a cellulose membrane.

23. The dynamic light scattering analyzer according to claim 10 wherein a gap in the range between about 0.5 to 5 millimeters is formed between said means for exposing said particles to a light source and said membrane.

24. The dynamic light scattering analyzer according to claim 10 further comprising a coaxial flow conduit disposed on the side of said membrane which is opposite said cell chamber.

25. The dynamic light scattering analyzer according to claim 24 wherein said coaxial flow conduit comprises an outer conduit centrally disposed about an inner conduit.

26. A photodetector probe assembly which is capable of measuring the size of particles contained within said photodetector probe assembly, said photodetector probe assembly comprises:

a housing;

a cell chamber disposed within the end of said housing which is in contact with a liquid carrier, wherein said cell chamber is formed by affixing a membrane to said end of said housing, said membrane is one which is capable of retaining therein particles of a sample contained within said cell chamber while allowing said liquid carrier to diffuse across said membrane in and out of said cell chamber;

a light source;

a means for exposing said particles to a light source, said means for exposing being disposed substantially opposite said membrane;

a means for receiving the light scattered from said particles within said cell chamber and the light reflected from the light source-sample interface; and a means of detecting the amount of light scattered from said particles within said cell chamber and light reflected from the light source-sample interface.

* * * * *